United States Patent

Cannata et al.

[11] Patent Number: 5,811,586
[45] Date of Patent: Sep. 22, 1998

[54] PROCESS FOR MANUFACTURING 1-(3-TRIFLUOROMETHYL)-PHENYL-PROPAN-2-ONE INTERMEDIATE IN THE SYNTHESIS OF THE FENFLURAMINE

[75] Inventors: Vincenzo Cannata, Bologna; Barbara Galbiati, Milan; Angelo Spreafico, Lecco, all of Italy

[73] Assignee: Alfa Chemicals Italiana S.P.A., Bergamo, Italy

[21] Appl. No.: 837,436

[22] Filed: Apr. 17, 1997

[30] Foreign Application Priority Data

May 29, 1996 [IT] Italy ................. BO96A0289

[51] Int. Cl.⁶ ..................... C07C 45/45
[52] U.S. Cl. ............. 568/322; 568/309; 568/323
[58] Field of Search .............. 568/309, 322, 568/323

[56] References Cited

U.S. PATENT DOCUMENTS 3,198,833  8/1965  Beregi et al. ................ 260/570.8

OTHER PUBLICATIONS

C.S. Rondestvedt, Jr., in Organic Reactions, Wiley, New York, vol. 24, Chapter 3, 1976.
Rondestvedt, Jr., Arylation of Unsaturated Systems by Free Radicals, Journal of American Chemical Society, &&, pp. 3401–3402, 1955.
Rondestvedt, Arylation of Unsaturated Compounds by Daizonium Salts, 1960.
Allard and Levisalles, Bulletin De La Societe Chimique De France, #5, pp. 1926–1931, 1972.
Raucher et al; Journal of Organic Chemistry; vol. 48, pp. 2066–2069, 1983.

*Primary Examiner*—Gary Geist
*Assistant Examiner*—Sreeni Padmanabhan
*Attorney, Agent, or Firm*—Bucknam and Archer

[57] ABSTRACT

A process for manufacturing 1-(3-trifluoromethyl)phenyl-propan-2-one intermediate in the synthesis of the anorexic drug fenfluramine consists of reacting the diazonium salt of 3-trifluoromethylaniline with isopropenyl acetate in a polar solvent in the presence of a catalytic amount of a cuprous salt and, optionally, of a base and purifying the crude product through the bisulfite complex or distillation under vacuum.

6 Claims, No Drawings

PROCESS FOR MANUFACTURING 1-(3-TRIFLUOROMETHYL)-PHENYL-PROPAN-2-ONE INTERMEDIATE IN THE SYNTHESIS OF THE FENFLURAMINE

BACKGROUND OF THE PRIOR ART

Fenfluramine is a known drug used to fight obesity described in U.S. Pat. No. 3,198,833.

It has been synthesized in many ways, some going through the synthesis of the intermediate (1-3 (trifluoromethyl)phenyl-propan-2-one. This U.S. Pat. No. 3,198,833 describes some syntheses of this Ketone starting from 3-trifluoromethylphenylacetonitrile or from the corresponding alcohol.

All these methods are not convenient from the economic and industrial point of view because of the very high cost and of the difficult availability of the starting compounds.

The process described in the present invention is a remarkable improvement of the above mentioned methods because the desired ketone is obtained with good yields starting from 3-trifluoromethylaniline, a product easily available and at an industrially accessible price.

Fenfluramine is obtained from 1-(3-trifluoromethyl) phenyl-propan-2-one through the known reaction of reductive amination, for instance as described in Hungarian Patent HU T055343, and therefore its synthesis does not form object of the present invention.

SUMMARY OF THE INVENTION

Object of the invention is a new process for the industrial manufacture of 1-(3-trifluoromethyl)phenyl-propan-2-one, intermediate in the synthesis of the anorexic drug fenfluramine.

This process consists of preparing the diazonium salt of the 3-trifluoromethylaniline and reacting this diazonium salt in a polar solvent with isopropenyl acetate in presence of a catalytic amount of a cuprous or cupric salt or of a mixture thereof and, optionally, of a base according to the following scheme:

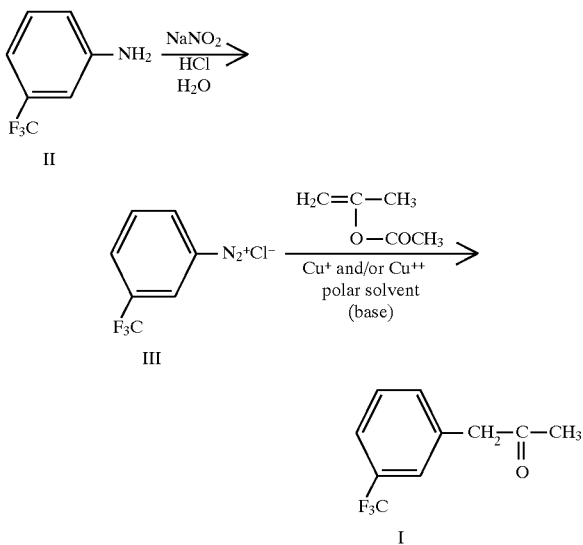

The crude reaction product, obtained in an oily form, is purified either by distillation under vacuum or by formation of the bisulfite complex followed by alkaline hydrolysis of such complex to restore the ketone.

The diazotation reaction is carried out by treating in water a molar equivalent of 3-trifluoromethylaniline of formula II with from 1.5 to 4 molar equivalents of hydrochloric acid in concentrated aqueous solution and with from 1 to 2 molar equivalents of sodium nitrite dissolved in water, at a temperature between 0° C. and 25° C. and for a period of time between 30 minutes and 3 hours. The so obtained diazonium salt of formula III is reacted, for a period of time between 30 minutes and 3 hours and at a temperature between 20° C. and 70° C., with a mixture containing from 1 to 3 molar equivalents of isopropenyl acetate, from 0.01 to 0.20 molar equivalents of a cuprous or cupric salt or of a mixture thereof and from 0 to 3 molar equivalents of a base in a polar solvent.

The crude reaction product is extracted from the reaction mixture by means of an organic solvent, for instance an alkyl halide, for instance methylene chloride, or a hydrocarbon, for instance heptane, and can be purified or by evaporation of the organic solvent and subsequent distillation under vacuum, keeping the fraction boiling at 98° C.–102° C. under a pressure of 10 mm Hg, or by formation and subsequent alkaline hydrolysis of the bisulfite complex.

Many cuprous or cupric salts like chlorides, bromides, sulfates, nitrates and acetates can be advantageously used as catalysts of the reaction between diazonium salt and isopropenyl acetate; the chlorides are particularly preferred in carrying out the invention.

The polar solvent may be water, acetone, an alcohol from 1 to 5 carbon atoms, acetonitrile, dioxane, N,N-dimethylformamide or mixtures thereof.

Mixtures of water with acetone or with an alcohol containing from 1 to 3 carbon atoms are preferred in carrying out the present invention.

Acetates, bicarbonates and carbonates of the alkali metals are the bases that may be advantageously used in carrying out the invention, sodium acetate and bicarbonate being mainly preferred.

The examples below reported constitute a further illustration of the invention and are not to be considered as an its limitation.

EXAMPLE 1

1-(3-Trifluoromethyl)phenyl-propan-2-one

35 Ml of water and 45 g of 37% (w/w) aqueous hydrochloric acid are put in a flask equipped with stirrer and dropping funnel. 24.25 Grams (0.151 moles) of m-trifluoromethylaniline are added after having cooled to 10° C. with an ice bath and then, at 5° C., an aqueous solution containing 12.43 g (0.180 moles) of sodium nitrite in 150 ml of water is slowly added. The reaction mixture is stirred for 30 minutes and then is poured during 30 minutes into a mixture made by 90 ml of water, 1.35 g (0.014 moles) of cuprous chloride, 2.30 g (0.013 moles) of cupric chloride dihydrate, 50 ml of acetone, 40.8 g (0.300 moles) of sodium acetate trihydrate and 23 g (0.230 moles) of isopropenyl acetate while keeping the reaction temperature at 30° C. After further 30 minutes of stirring, the reaction mixture is brought to 20° C., 50 ml of methylene chloride are added and the two layers are separated.

The aqueous layer is discarded while the organic layer is concentrated under vacuum until an oil is obtained which is treated with 35 g of sodium metabisulfite, 70 ml of water and 150 ml of heptane under stirring at room temperature for 12 hours. The suspension is filtered, the bisulfite complex is washed on the filter with 50 ml of heptane and then suspended in a two-phase mixture made by 100 ml of methylene chloride and 150 ml of a 10% (w/v) aqueous solution of sodium hydroxide. The layers are separated after one hour of stirring at room temperature, the aqueous phase is discarded while the organic layer is washed with water and evaporated under vacuum to give 12 g of pure ketone with a yield equal to 39% calculated on the starting m-trifluoromethylaniline.

EXAMPLE 2

1-(3-Trifluoromethyl)phenyl-propan-2-one 200 ml of water and 180 g of 37% (w/w) aqueous hydrochloric acid are put in a flask equipped with stirrer and dripping funnel. 97 Grams (0.602 moles) of m-trifluoromethylaniline are added after having cooled to 10° C. with an ice bath and then, at 5° C., an aqueous solution containing 49.80 g (0.722 moles) of sodium nitrite in 170 ml of water is slowly added. The reaction mixture is stirred for 30 minutes and then is added during 30 minutes to a mixture of 520 ml of water, 18.40 g (0.108 moles) of cupric chloride dihydrate, 280 ml of acetone, 81.60 g (0.600 moles) of sodium acetate trihydrate and 75.20 g (0.751 moles) of isopropenyl acetate while keeping the reaction temperature at 30° C. After further 30 minutes of stirring at 40° C., the reaction mixture is brought to 20° C., 300 ml of methylene chloride are added and the two layers are separated.

The aqueous layer is discarded while the organic layer is concentrated under vacuum until is obtained an oil which is treated with 100 g of sodium metabisulfite, 200 ml of water and 400 ml of heptane under stirring at room temperature for 12 hours. The suspension is filtered, the bisulfite complex is washed on the filter with 150 ml of heptane and then suspended in a two-phase mixture consisting of 300 ml of methylene chloride, 480 ml of water and 130 ml of a 30% (w/v) aqueous solution of sodium hydroxide. The layers are separated after one hour under stirring at room temperature, the aqueous layer is discarded while the organic layer is washed with water and evaporated under vacuum to give 52 g of pure ketone with a yield equal to 42.7% calculated on the starting m-trifluoromethylaniline.

EXAMPLE 3

1-(3-Trifluoromethyl)phenyl-propan-2-one

220 Ml of water and 180 g of 37% (w/w) aqueous hydrochloric acid are put into a flask equipped with stirrer and dripping funnel. 97 Grams (0.602 moles) of m-trifluoromethylaniline are added after having cooled to 10° C. with an ice bath and then, at 5° C., an aqueous solution containing 42.2 g (0.612 moles) of sodium nitrite in 50 ml of water is slowly added. The reaction mixture is stirred for 30 minutes and then is added during 30 minutes to a mixture warmed at 40° C. made by 800 ml of water, 280 ml of methanol, 1.50 g (0.015 moles) of cuprous chloride, 49.2 g (1.200 moles) of anhydrous sodium acetate and 75.2 g (0.751 moles) of isopropenyl acetate.

The reaction temperature goes up till a maximum value of 60° C. and other 1.50 g (0.015 moles) of cuprous chloride are added after one half of the solution of the diazonium salt has been added. The reaction mixture is kept under stirring for another 30 minutes and then is cooled to 20° C. is added to 350 ml of heptane and the two layers are separated. The aqueous layer is discarded while the organic layer is washed with water, added to 100 g of sodium metabisulfite and of 200 ml of water and is kept under stirring at room temperature for 12 hours. The suspension is filtered, the bisulfite complex is washed on the filter with 150 ml of heptane and then suspended in a two-phase mixture made by 300 ml of heptane, 480 ml of water and 130 ml of a 30% (w/v) aqueous solution of sodium hydroxide. The layers are separated after one hour of stirring at room temperature, the aqueous layer is discarded while the organic layer is washed with water and evaporated under vacuum to give 70 g of pure ketone with a yield equal to 57.3% calculated on the starting m-trifluoromethylaniline.

EXAMPLE 4

1-(3-Trifluoromethyl)phenyl-propan-2-one 220 ml of water and 180 g of 37% (w/w) aqueous hydrochloric acid are put in a flask equipped with stirrer and dripping funnel. 97 Grams (0.602 moles) of m-trifluoromethylaniline are added after having cooled to 10° C. with an ice bath and then, at 5° C., an aqueous solution containing 42.2 g (0.612 moles) of sodium nitrite in 50 ml of water is slowly added. The reaction mixture is stirred for 30 minutes and then is added during 30 minutes to a mixture warmed at 40° C. consisting of 800 ml of water, 280 ml of methanol, 1.50 g (0.015 moles) of cuprous chloride, 49.2 g (1.200 moles) of anhydrous sodium acetate and 75.2 (0.751 moles) of isopropenyl acetate.

The reaction temperature goes up till a maximum value of 60° C., the reaction mixture is kept under stirring for further 30 minutes at this temperature and then is cooled to 20° C. 350 ml of heptane are added and the two layers are separated. The aqueous layer is discarded while the organic layer is washed with water and concentrated under vacuum to remove the solvent. The obtained oil is distilled under vacuum at 10 mm Hg collecting the fraction that distils at 98°÷102° C. 72 Grams of pure ketone are obtained with a yield equal to 59.1% calculated on the starting m-trifluoromethylaniline.

EXAMPLE 5

1-(3-Trifluoromethyl)phenyl-propan-2-one 220 ml of water and 145 ml of 30% (w/w) aqueous hydrochloric acid are put in a flask equipped with stirrer and dripping funnel. 97 Grams (0.602 moles) of m-trifluoromethylaniline are added after having cooled to 10° C. with an ice bath and then, at 5° C., an aqueous solution containing 42.2 g (0.612 moles) of sodium nitrite in 150 ml of water is slowly added. The reaction mixture is stirred for 30 minutes and then is added during 30 minutes to a mixture warmed at 40° C. consisting of 800 ml of water, 280 ml of methanol, 1.50 g (0.015 moles) of cuprous chloride and 75.2 g (0.751 moles) of isoprophenyl acetate.

The reaction temperature goes up till a maximum value of 60° C., the reaction mixture is kept under stirring for further 30 minutes at this temperature and then is cooled to 20° C. 350 ml of heptane are added and the two layers are separated. The aqueous layer is discarded while the organic layer is washed with water.

The product is purified through the bisulfite complex as hereinabove described. 57 Grams of pure ketone are obtained with a yield equal to 46.8% calculated on the starting m-trifluoromethylaniline.

EXAMPLE 6

1-(3-Trifluoromethyl)phenyl-propan-2-one 220 ml of water and 224 g of 30% (w/w) aqueous hydrochloric acid are put in a flask equipped with stirrer and dripping funnel. 97 Grams (0.602 moles) of m-trifluoromethylaniline are added after having cooled to 10° C. with an ice bath and then, at 5° C., an aqueous solution containing 49.80 g (0.722 moles) of sodium nitrite in 180 ml of water is slowly added. The reaction mixture is stirred for 30 minutes and then is added during 30 minutes to a mixture warmed at 40° C. consisting of 450 ml of water, 151.2 g (1.800 moles) of sodium bicarbonate, 280 ml of methanol, 1.50 g (0.015 moles) of cuprous chloride and 75.2 g (0.751 moles) of isopropenyl acetate.

The reaction temperature goes up till a maximum value of 60° C., the reaction mixture is kept under stirring for further 30 minutes at this temperature then is cooled to 20° C. 350 ml of heptane are added and the two layers are separated. The aqueous layer is discarded while the organic layer is washed with water.

The product is purified through bisulfite complex as before described. 51 Grams of pure ketone are obtained with a yield equal to 41.9% calculated on the starting m-trifluoromethylaniline.

We claim:

1. In the process of preparation of a Ketone substituted by a phenyl ring and said phenyl ring is substituted by an electron withdrawing group and the process is carried out by reaction of the diazonium salt of a phenylamine substituted by an electron withdrawing group with an unsaturated acceptor, the improvement wherein the diazonium salt of 3-trifluoromethyl aniline is reacted with isopropenyl acetate in aqueous methanol in the presence of cuprous chloride as a catalyst and sodium acetate as a base at a temperature up to 60° C., and after cooling heptane is added, the aqueous layer is discarded and the product 1-(3-trifluoromethyl) phenyl-propan-2-one of boiling point of 98°–102° C. is obtained by vacuum distillation on through the bisulfite complex.

2. A process for the production of 1-(3-trifluoromethyl) phenyl-propan-2-one of formula I

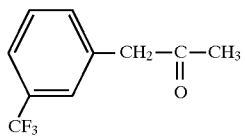

which consists of a) diazotizing one molar equivalent of trifluoromethylaniline of formula II

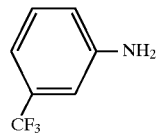

in 1.5–4 molar equivalents of aqueous hydrochloric acid by reaction with 1–2 molar equivalents of sodium nitrite dissolved in water, to produce the diazonium salt of formula III

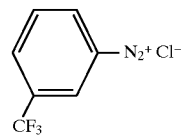

b) reacting said diazonium salt of formula III with 1–1.5 molar equivalent of isopropenyl acetate dissolved in an alcohol containing 1–3 carbon atoms, in the presence of a catalytic amount of 0.015–0.03 molar equivalent of cuprous chloride, in the absence of a base or in the presence of a base in the amount up to 3 molar equivalents, at a temperature up to 60° C. whereby an oil of crude 1-(3-trifluoromethyl)-phenyl-propan-2-one is obtained c) purifying said oil from step b) by vacuum distillation or through the bisulfite complex to obtain the pure product of formula I.

3. The process according to claim 2 wherein said alcohol is methanol.

4. The process according to claim 2 wherein said base is sodium acetate in the amount of two molar equivalents.

5. The process according to claim 2 wherein the base is sodium bicarbonate in the amount of three molar equivalents.

6. The process according to claim 2 wherein the amount of cuprous chloride is 0.03 molar equivalents.

* * * * *